United States Patent [19]

Higgins, Jr. et al.

[11] Patent Number: 4,548,925

[45] Date of Patent: Oct. 22, 1985

[54] ANTIBIOTIC M43A, PHARMACEUTICAL COMPOSITION AND METHOD OF USE

[75] Inventors: Harvey M. Higgins, Jr., Danville; Kurt E. Merkel, Mooresville, both of Ind.; Mack H. McCormick, Florence, Oreg.

[73] Assignee: Eli Lilly and Company, Indianapolis, Ind.

[21] Appl. No.: 600,729

[22] Filed: Apr. 16, 1984

[51] Int. Cl.$^4$ .................... A61K 37/02; A61K 31/71; C07H 15/20

[52] U.S. Cl. .............................. 514/10; 260/112.5 R; 514/25; 514/53; 536/16.8; 536/18.1

[58] Field of Search ............................ 536/16.8, 18.1; 424/181, 77; 260/112.5 R; 514/53, 25, 10

[56] References Cited

U.S. PATENT DOCUMENTS 3,067,099  12/1962  McCormick et al. ................ 167/65

OTHER PUBLICATIONS

Donald J. McGraw, "The Antibiotic Discovery Era, (1940–1960); Vancomycin as an Example of the Era," Thesis at Oregon State University, 1975, pp. 78–142.

F. J. Marshall, "Structure Studies on Vancomycin," *J. Med. Chem.* 8, 18–22, (1965).

G. M. Sheldrick et al., "Structure of Vancomycin and its Complex with Acetyl-D-alanyl-D-alanine," *Nature* 271, 223–225, (1978).

C. M. Harris, et al., "Structure of the Glucopeptide Antibiotic Vancomycin, Evidence for an Asparagine Residue in the Peptide," *J. Am. Chem. Soc.*, 104, pp. 4293–4295.

"Vancomycin and Factor A," Report by Eli Lilly and Company sent to the U.S. Food and Drug Administration on Mar. 5, 1963.

G. K. Best et al., "Chromatographic Separation of the Vancomycin Complex," *Antimicrob. Agents & Chemotherapy*—1968, 115–119.

R. R. Pfeiffer, "Structural Features of Vancomycin," in *Reviews of Infectious Diseases*, vol. 3 Supplement, (1981).

*Primary Examiner*—Johnnie R. Brown
*Attorney, Agent, or Firm*—Nancy J. Harrison; Arthur R. Whale

[57] ABSTRACT

Antibiotic M43A, a new glycopeptide antibiotic of the vancomycin class, is produced by *Nocardia orientalis* strains NRRL 2450 and NRRL 2452. M43A has excellent antibacterial activity comparable to that of vancomycin.

6 Claims, No Drawings

ANTIBIOTIC M43A, PHARMACEUTICAL COMPOSITION AND METHOD OF USE

SUMMARY OF THE INVENTION

Antibiotic M43A is a new glycopeptide antibiotic produced by *Nocardia orientalis* NRRL 2450 and *N. orientalis* NRRL 2452. Antibiotic M43A and its salts have excellent activity against gram-positive microorganisms.

DETAILED DESCRIPTION

This invention relates to a new antibiotic called M43A, and to its salts. M43A has structural formula 1:

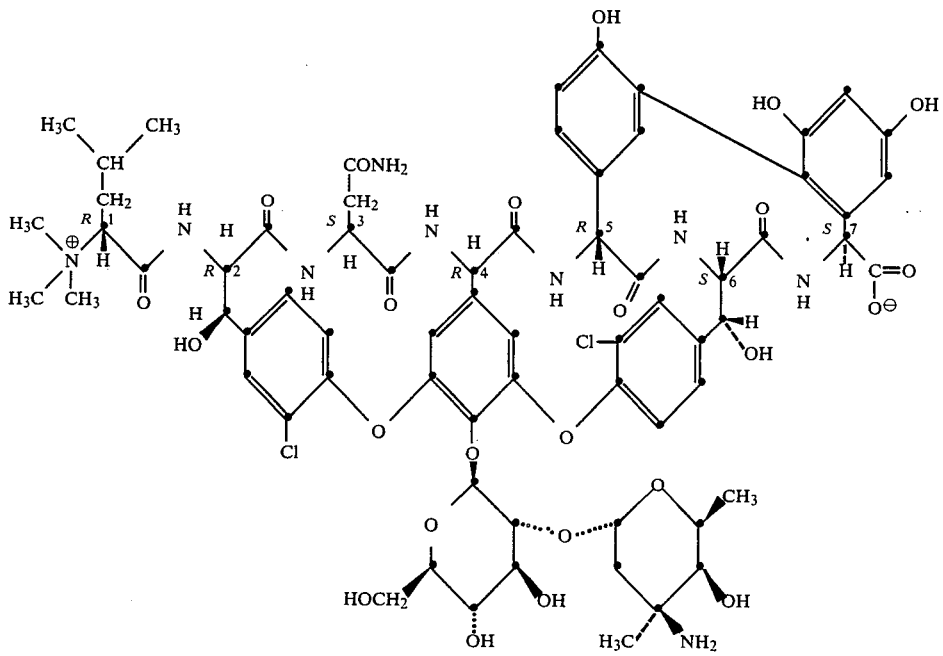

Antibiotic M43A and its salts have excellent antibacterial activity. The pharmaceutically acceptable salts of M43A are especially useful.

New, improved antibiotics are continually in demand, particularly for the treatment of human diseases. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

In the search for new antibiotics, structural modification of known antibiotics is attempted whenever possible. This approach is limited, however, to modifications which retain the desired activity. Many antibiotics, including the glycopeptides, have such complex structures that even small changes can be difficult to make by chemical means. The discovery of new antibiotics produced by fermentation processes continues, therefore, to be of great importance even in cases where the antibiotic, once recognized, is quite similar to a previously known antibiotic.

Antibiotic M43A is a newly discovered member of the glycopeptide group of antibiotics. Closely related members of this group include vancomycin (see, for example, U.S. Pat. No. 3,067,099), ristocetin, antibiotic A51568 factors A and B (see the copending applications of M. M. Hoehn and G. G. Marconi, Ser. No. 562,255, filed Dec. 16, 1983, and LaVerne D. Boeck et al., Ser. No. 561,008, filed Dec. 13, 1983).

In U.S. Pat. No. 3,067,099, McCormick et al. described the preparation of vancomycin. Three strains of *Streptomyces orientalis*, two of which were numbered M43-05865 and M5-18260, were disclosed as being capable of making vancomycin. The cultures were deposited at what was then the Northern Regional Research Laboratories at Peoria, Ill., given the accession numbers NRRL 2450 (M43-05865) and NRRL 2452 (M5-18260). Later, the organism designation for the strains was changed from *Streptomyces orientalis* to *Nocardia orientalis*.

The vancomycin described in U.S. Pat. No. 3,067,099 became an important, commercially available antibiotic. The *N. orientalis* culture used to prepare commercial product was *N. orientalis* strain M5-18260 (NRRL 2452) or its progeny.

The structure of a closely related derivative of vancomycin was determined by Sheldrick et al [G. M. Sheldrick, P. G. Jones, O. Kennard, D. H. Williams and G. A. Smith, *Nature* 271 (5642), 223–225 (1978)]; later, the structure of vancomycin itself was found by Harris et al. [C. M. Harris and T. M. Harris, *J. Am. Chem. Soc.* 104, 4293–4295 (1982)] to be that shown in formula 2:

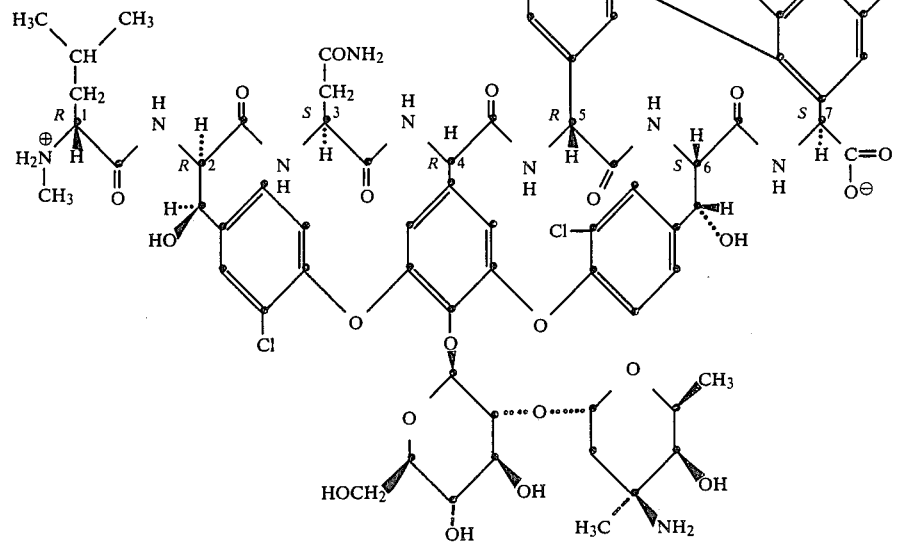

2

We have discovered that the *N. orientalis* M5-18260 (NRRL 2452) strain produces very small amounts of M43A. Later, M. M. Hoehn and R. Nagarajan discovered that, in addition to vancomycin, the antibiotic complex produced by *N. orientalis* M43-05865 (NRRL 2450), the M43 antibiotic complex, contained antibiotic M43A. This discovery is the subject of their copending application entitled METHOD FOR PRODUCING M43 ANTIBIOTICS, Ser. No. 600,728, filed herewith this even date. The ratio of M43A to vancomycin produced by the M43-05865 strain is approximately 2.5 to 1. In addition, the M43 complex contains a number of minor factors. Among the minor M43A factors are (1) A51568 factor A of Hoehn and Marconi, supra, and possibly A51568 factor B of Boeck et al., supra; (2) antibiotic M43D, which is the subject of a copending application of Kurt Merkel entitled ANTIBIOTIC M43 D, Ser. No. 600,725, filed herewith this even date; (3) the compounds designated agluco-A51568A, aglucovancomycin and algluco-M43A, and possibly desvancosaminevancomycin, all of which are disclosed in the copending application of R. Nagarajan and A. Schabel entitled NOVEL GLYCOPEPTIDE ANTIBIOTICS, Ser. No. 600,727, also filed herewith this even date; and (4) antibiotic M43C and possibly antibiotic M43B, both of which are disclosed in the copending application of Karl H. Michel entitled ANTIBIOTICS M43B AND M43C, Ser. No. 600,726, also filed herewith this even date. The structural relationships of this group of antibiotics are provided in formulas 1-12 which follow:

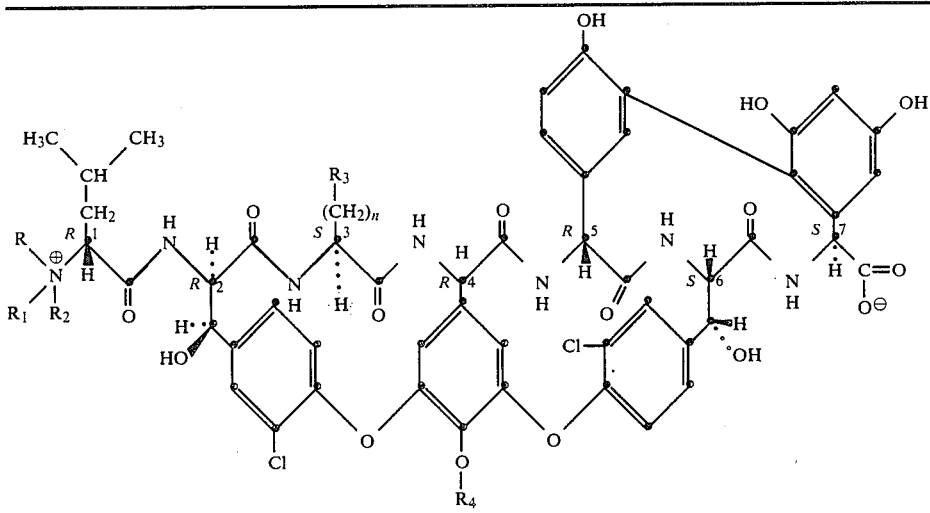

| Compound No. | Compound | R | $R_1$ | $R_2$ | $R_3$ | n | $R_4$ |
|---|---|---|---|---|---|---|---|
| 1 | M43A | $CH_3$ | $CH_3$ | $CH_3$ | $CONH_2$ | 1 | vancosaminyl-O—glucosyl |
| 2 | Vancomycin | H | H | $CH_3$ | $CONH_2$ | 1 | vancosaminyl-O—glucosyl |
| 3 | M43B | $CH_3$ | $CH_3$ | $CH_3$ | COOH | 1 | vancosaminyl-O—glucosyl |

-continued

| | | | | | | | | |
|---|---|---|---|---|---|---|---|---|
| 4 | M43C | $CH_3$ | $CH_3$ | $CH_3$ | $CONH_2$ | 1 | glucosyl |
| 5 | M43D | H | $CH_3$ | $CH_3$ | $CONH_2$ | 1 | vancosaminyl-O—glucosyl |
| 6 | Agluco-A51568A | H | H | H | $CONH_2$ | 1 | H |
| 7 | Aglucovancomycin | H | H | $CH_3$ | $CONH_2$ | 1 | H |
| 8 | Agluco-M43A | $CH_3$ | $CH_3$ | $CH_3$ | $CONH_2$ | 1 | H |
| 9 | Desvancosamine-A51568A | H | H | H | $CONH_2$ | 1 | glucosyl |
| 10 | Desvancosamine-Vancomycin | H | H | $CH_3$ | $CONH_2$ | 1 | glucosyl |
| 11 | A51568A | H | H | H | $CONH_2$ | 1 | vancosaminyl-O—glucosyl |
| 12 | A51568B | H | H | H | $CONH_2$ | 2 | vancosaminyl-O—glucosyl |

M43A, the new glycopeptide antibiotic of this invention, is very close to vancomycin in structure and also in activity. It is, therefore, a valuable addition to this group of antibiotics.

M43A is shown in formula 1 as a zwitterion. Those in the art will recognize, however, that M43A has a carboxyl group, two amino groups and three phenolic groups which can react to form various salts. All such forms of M43A are part of this invention. M43A salts are useful, for example, for separating and purifying M43A. In addition, the salts have an improved solubility in water.

M43A salts are prepared using standard procedures for salt preparation. For example, the M43A zwitterion can be neutralized with an appropriate acid to form an M43A acid addition salt.

The acid addition salts of M43A are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicyclic, methanesulfonic, benzenesulfonic, sorbic, picric, benzoic, cinnamic and like acids.

Pharmaceutically acceptable acid addition salts are an especially preferred group of salts of this invention.

Antibiotic M43A is prepared by culturing *Nocardia orientalis* NRRL 2450 or NRRL 2452, or an M43A-producing variant, mutant or recombinant thereof, under submerged aerobic conditions in a suitable culture medium until a substantial amount of M43A is produced. The culture medium used to grow *Nocardia orientalis* NRRL 2450 or NRRL 2452 can be one of a number of media. For economy in production, optimal yield, and ease of product isolation, however, certain culture media are preferred. Thus, for example, preferred carbon sources include carbohydrates such as dextrin, dextrose, glucose and glycerol. Preferred nitrogen sources include enzyme digests of casein, cottonseed meal, soybean grits, protein peptones and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of antibiotic M43A, submerged aerobic fermentation in tanks is preferred. Small quantities may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

*N. orientalis* NRRL 2450 or NRRL 2452 can be grown at temperatures between about 25° and about 37° C. Optimum antibiotic production appears to occur at temperatures of about 30° C.

As is customary in aerobic submerged culture processes, sterile air is bubbled through the culture medium. For efficient antibiotic production the percent of air saturation for tank production should be about 50% or above (at 30° C. and about 5 psi of back pressure).

Antibiotics production can be followed during the fermentation by testing samples of the broth against organisms known to be sensitive to antibiotic M43A. One useful assay organism is *Staphylococcus aureus* NRRL B313. In addition, antibiotic production can be monitored by HPLC with UV detection.

Following its production under submerged aerobic fermentation conditions, antibiotic M43A can be recovered from the fermentation medium by filtering the broth to remove mycelia and purifying the filtered broth by a series of adsorptions on suitable adsorbents, such as an ion-exchange resins, chemically modified hydrophobic inorganic supports used in high performance reverse-phase liquid chromatography, and high porosity polymers, eluting the M43A in each case with a suitable solvent such as aqueous acetonitrile.

M43A inhibits the growth of a broad spectrum of pathogenic bacteria, especially gram-positive bacteria. Table I summarizes the minimal inhibitory concentrations (MIC's) at which M43A inhibits certain organisms, as determined by standard agar-dilution assays. In Table I the activity of M43A (phosphate salt) is compared with that of vancomycin (free base).

TABLE I

In Vitro Activity of M43A

| | MIC (mcg/ml) | |
|---|---|---|
| Organism | Vancomycin | M43A |
| *Staphylococcus aureus* NRRL B313 | 1 | 1 |
| *Staphylococcus aureus* V41 | 1 | 1 |
| *Staphylococcus aureus* X400 | 1 | 2 |
| *Staphylococcus aureus* S13E | 1 | 1 |
| *Staphylococcus epidermidis* EPI1 | 2 | 4 |
| *Staphylococcus epidermidis* 222 | 1 | 2 |
| *Streptococcus pyogenes* C203 | 1 | 1 |
| *Streptococcus pneumoniae* Park 1 | 0.5 | 0.5 |
| *Streptococcus faecium* ATCC 9790 | 1 | 1 |
| Streptococcus sp. group D 9960 | 4 | 4 |
| *Haemophilus influenzae* C.L. | 128 | 64 |

TABLE I-continued

In Vitro Activity of M43A

| Organism | MIC (mcg/ml) | |
|---|---|---|
| | Vancomycin | M43A |
| Haemophilus influenzae 76 | 32 | 64 |
| Escherichia coli N10 | >128 | >64 |
| Escherichia coli EC14 | >128 | >64 |
| Escherichia coli TEM | >128 | >64 |
| Klebsiella pneumoniae X26 | >128 | >64 |
| Klebsiella pneumoniae X68 | >128 | >64 |
| Klebsiella pneumoniae KAE | >128 | >64 |

M43A also inhibits the growth of anaerobic bacteria. Table II summarizes the susceptibility of various anaerobic isolates to M43A.

TABLE II

Susceptibility of Anaerobic Bacterial Isolates to M43A

| ANAEROBIC BACTERIA | MIC ($\mu$g/ml)[a] | |
|---|---|---|
| | Vancomycin | M43A |
| Clostridium difficile 2994 | 2 | 1 |
| Clostridium perfringens 81 | 1 | 1 |
| Clostridium septicum 1128 | 4 | 32 |
| Eubacterium aerofaciens 1235 | 16 | 4 |
| Peptococcus asaccharolyticus 1302 | 2 | 2 |
| Peptococcus prevoti 1281 | 2 | 1 |
| Peptostreptococcus anaerobius 1428 | 2 | 0.5 |
| Peptostreptococcus intermedius 1264 | 4 | 8 |
| Propionibacterium acnes 79 | 2 | 1 |
| Bacteroides fragilis 111 | 64 | 8 |
| Bacteroides fragilis 1877 | 32 | <0.125 |
| Bacteroides fragilis 1936B | 32 | 2 |
| Bacteroides thetaiotaomicron 1438 | 16 | 8 |
| Bacteroides melaninogenicus 1856/28 | >128 | ≦0.125 |
| Bacteroides melaninogenicus 2736 | 8 | ≦0.125 |
| Bacteroides vulgatis 1211 | 16 | ≦0.125 |
| Bacteroides corrodens 1874 | 32 | ≦0.125 |
| Fusobacterium symbiosum 1470 | 2 | ≧0.125 |
| Fusobacterium necrophorum 6054A | 2 | 2 |

[a]MIC's were determined by the agar-dilution method; endpoints were read after 24-hrs. incubation.

M43A has also shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., J. Bacteriol. 81, 233-235 (1961)]. $ED_{50}$ values observed for M43A are given in Table III.

TABLE III

| | $ED_{50}$ Values for M43A | | |
|---|---|---|---|
| Organism | Route of Administration | $E_{50}$ (mg/kg/2) | |
| | | Vancomycin | M43A |
| Staphylococcus aureus | subcutaneous | 1.62 | 0.5 |
| Streptococcus pyogenes | " | 1.2 | 1.36 |
| Streptococcus pneumoniae | " | 1.47 | 0.88 |

Pharmaceutical formulations of M43A or salts of M43A (an M43A compound) are also part of this invention. M43A, preferably as a pharmaceutically acceptable salt, can be formulated for oral or parenteral administration for the therapeutic or prophylactic treatment of bacterial infections. For example, an M43A compound can be admixed with conventional pharmaceutical carriers and excipients and used in the form of tablets, capsules, elixirs, suspensions, syrups, wafers and the like. The compositions comprising an M43A compound will contain from about 0.1 to about 90% by weight of the active compound, and more generally from about 10 to about 30%. The compositions may contain common carriers and excipients, such as corn starch or gelatin, lactose, sucrose, microcrystalline cellulose, kaolin, mannitol, dicalcium phosphate, sodium chloride and alginic acid. Disintegrators commonly used in the formulations of this invention include croscarmellose sodium, microcrystalline cellulose, corn starch, sodium starch glycolate and alginic acid. Tablet binders that can be included are acacia, methylcellulose, sodium carboxymethylcellulose, polyvinylpyrrolidone (Providone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of M43A, for example the hydrochloride salt, can be dissolved and administered in a pharmaceutical diluent such as Water-for-Injection, physiological saline or 5% glucose. A suitable insoluble form of M43A may be prepared and administered as a suspension in an aqueous base or a pharmaceutically acceptable oil base, e.g. an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic or preferably a salt thereof in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating or controlling infectious diseases, especially those caused by gram-positive microorganisms, in animals. This method comprises administering to the animal an effective dose of the antibiotic. An effective dose is generally between about 0.5 and about 100 mg/kg of M43A or a pharmaceutically acceptable salt of M43A. A preferred dose is from about 10 to about 60 mg/kg of M43A compound. A typical daily dose for an adult human is from about 250 mg to about 1.0 g.

In practicing this method, the antibiotic can be administered in a single daily dose or in multiple doses per day. The treatment regime may require administration over extended periods of time, e.g., for several days or for from two to three weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the threatment method is to administer the antibiotic via IV infusion. In this procedure a sterile formulation of a suitable soluble salt of the antibiotic is incorporated in a solution of a physiological fluid, such as 5% dextrose solution, and the resulting solution is infused slowly IV. Alternatively, the piggy-back method of IV infusion can be used.

In another embodiment, this invention relates to methods of increasing feed-utilization efficiency in poultry, swine, sheep and cattle, of promoting growth rates in cattle raised for meat production and of enhancing milk production in lactating ruminants. For increasing feed utilization efficiency and promoting growth, an M43A compound is administered orally in a suitable feed in an amount of from about 2 to about 200 grams per ton of total feed. For beef cattle, for example, a range of about 12 to 3000 mg/head/day is suitable. For enhancing milk production in lactating ruminants, oral administration of a daily amount of from about 0.04 to about 16 mg/kg of body weight (or about 25 to about 5000 mg/ruminant/day) is suggested.

The following examples are provided to illustrate this invention:

EXAMPLE 1

Isolation of Antibiotic M43A from *N. orientalis* NRRL 2452

A. Separation from Vancomycin

Using the procedure in U.S. Pat. No. 3,067,099 (Example 2), fourteen 1200 gallon fermenters were processed to give a crude preparation in the hydrochloride salt form. This preparation was further separated on a Dowex 50-2X resin column, selectively eluting fractions containing M43A with a 2-percent aqueous ammonium formate solution (pH 9.6) as the eluent, to give a semi-purified prepartion containing M43A.

B. Purification of M43A

A portion of the M43A-enriched material (1.0–1.3 g) was suspended in deionized water. The pH of the resulting suspension was adjusted to pH 3 with 10% aqueous phosphoric acid. The resulting solution, diluted to a volume of 10 ml, was passed through a .45-$\mu$m membrane filter (Millex-HA 0.45-$\mu$m filter unit, Millipore Corporation, Bedford, MA, 01730). The filtrate was separated in two-ml portions through a chromatography column (37×350 mm) containing LiChroprep ® RP-18 (15–25 $\mu$m (Art. #13901, E. Merck, Darmstadt, Germany) as the stationary phase. The column was eluted with an aqueous acetonitrile gradient containing 12–20% of acetonitrile. The aqueous phase of the gradient contained triethylamine (0.2%) and was adjusted (prior to the acetonitrile addition) to pH 3 with 10% aqueous phosphoric acid. The column effluent was monitored by UV activity and fractions were combined accordingly. The M43A-containing fractions from eighteen such separations were combined. The acetonitrile was removed by evaporation under high vacuum, and the aqueous solution was concentrated to one-tenth of the original volume. The concentrated aqueous solution was loaded on a column (15×275 mm) containing freshly conditioned Diaion HP-20 resin (Mitsubishi Chemical Industries Limited, Tokyo 100, Japan). The column was extensively washed with water and then was eluted with water containing 25–50% methanol. The methanol was removed under high vacuum, and the resulting aqueous solution was evaporated to dryness. M43A was obtained as a dry amorphorus solid (0.6 g).

C. Characteristics of M43A

M43A has an integer molecular weight of 1475 as determined by fast-atom-bombardment mass spectrometry. The molecular weight of M43A is 28 units higher than that of vancomycin (m.w. 1447).

The molecular structure of M43A, as shown in formula 1, was deduced from X-ray diffraction studies on a closely-related derivative.

The proton NMR assignments for M43A are summarized in Table IV. The chemical shifts listed in Table IV were obtained in DMSO-$d_6$ solution at 60° C. and at 360 MHz proton frequency. The numbering scheme used is shown in formula 13:

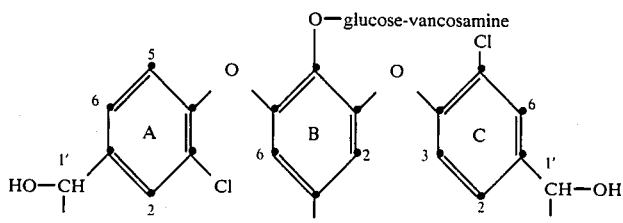

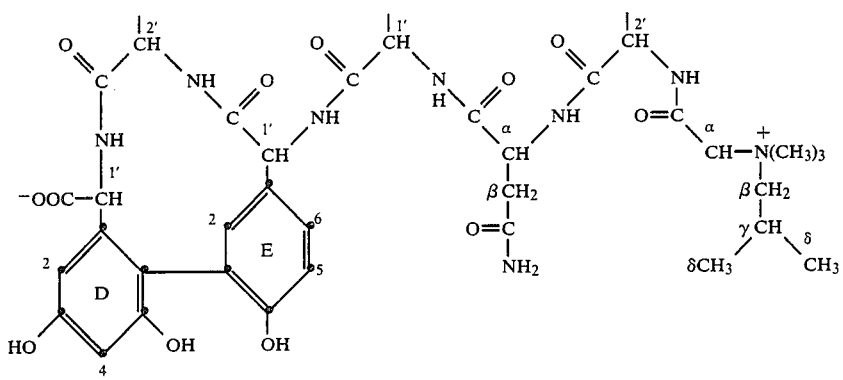

TABLE IV

| Proton NMR Assignments for M43A[a] | |
|---|---|
| Assignment | Chem. Shift |
| A-NH | 6.46 |
| A-2' | 4.17 |
| A-1' | 5.14 |
| A-1'(OH) | 5.86 |
| A-2 | 7.88 |
| A-5 | 7.28 |
| A-6 | 7.45 |
| B-NH | 8.59 |
| B-1' | 5.77 |
| B-2 | 5.69 |
| B-6 | 5.19 |
| C-NH | 9.49 |
| C-2' | 4.84 |
| C-1' | 5.19 |
| C-1'(OH) | |
| C-2 | 7.55 |
| C-3 | 7.16 |
| C-6 | 7.61 |
| D-NH | 8.39 |
| D-1' | 4.44 |
| D-2 | 6.35 |
| D-4 | 6.38 |
| E-NH | 8.58 |
| E-1' | 4.47 |
| E-2 | 7.15 |
| E-5 | 6.70 |
| E-6 | 6.77 |
| Asn—NH | ~6.3 |
| Asn—α | 4.15 |
| Asn—β's | 2.73 and 2.10 |
| Asn—C(=O)—NH₂ | 7.45 and |
| | 6.99 |
| Leu—N(CH₃)₃⁺ | 3.20 |
| Leu—α | 4.43 |
| Leu—β's | 1.92 and 1.65 |
| Leu—γ | 1.53 |
| Leu—δ's | 0.97 and 0.90 |
| Glucose | |
| #1 | 5.33 |
| #2 | 3.59 |
| #3 | 3.46 |
| #4 | |
| #5 | |
| #6 | 3.57 and 3.70 |
| Vancosamine | |
| #1 | 5.27 |
| #2 | 1.84 and 1.65 |
| #3(CH₃) | 1.28 |
| #4 | |
| #5 | 4.64 |
| #6(CH₃) | 1.06 |

[a] Phenols not yet assigned

EXAMPLE 2

Isolation of M43A from *N. orientalis* M43-05865

A. Shake-flask Fermentation

A lyophilized pellet of *Nocardia orientalis* M43-05865 (NRRL 2450) is dispersed in 1-2 ml of sterilized water. This solution (<0.1 ml) is used to inoculate an agar slant having the following composition:

| Ingredient | Amount (g/L.) |
|---|---|
| Dextrin | 10 |
| Enzymatic hydrolysate of casein[a] | 2 |
| Beef extract | 1 |
| Yeast extract | 1 |
| Agar | 20 |
| Distilled water | q.s. to 1 liter |

[a] N—Z Amine A. Humko Sheffield Chemical, Lyndhurst NJ

The inoculated slant is incubated at 30° C. for 4-6 days. The mature slant culture is covered with sterile distilled water and scraped with a loop to loosen the spores. The resulting spore suspension (1 ml) is used to inoculate 100 ml of a vegetative medium having the following composition:

| Ingredient | Amount (g/L.) |
|---|---|
| Glucose | 15 |
| Soybean meal | 15 |
| Cornsteep solids | 5 |
| CaCO₃ | 2 |
| NaCl | 5 |
| Tap H₂O | q.s. to 1 liter |

The inoculated vegetative medium is incubated in a 500-ml Erlenmeyer flask for 24-48 hours at 30° C. on a reciprocal shaker with a 2-inch stroke at 108 RPM or on a rotary shaker operating at 250 RPM.

This incubated vegetative medium (5 ml) is used to inoculate 100 ml of a sterilized (120° C. for 30 minutes) production medium having the following composition:

| Ingredient | Amount (g/L.) |
|---|---|
| Glucose | 10 |
| Edible molasses | 20 |
| Peptone[a] | 5 |
| CaCO$_3$ | 2 |
| Tap H$_2$O | q.s. to 1 liter |

[a]Bacto (Difco Laboratories, Detroit, MI)

The inoculated fermentation medium is incubated in a 500-ml Erlenmeyer flask at 25°–30° C. for 72–96 hours on either a rotary shaker operating at 250 RPM or a reciprocal shaker operating at 108 strokes per minute. The pH of the uninoculated medium varies with the medium used for production, but the production media of Examples 2–5 have an initial pH range of 6.0 to 7.5 and a harvest pH range of 6.5 to 8.0.

B. Isolation of M43 Complex

Whole broth (2 L.), prepared as described in Section A, was filtered. The filtrate was treated with a cation exchange resin (Dowex 50WX4, H+, NH$_4$+, pH 5.0), using 100-ml of resin and stirring batchwise for 30 minutes. The effluent was decanted and discarded. The resin was washed thoroughly with water, and the water wash was discarded. The resin was then eluted batchwise with 1N NH$_4$OH (250 ml and 175 ml per batch). The eluates were combined and concentrated under vacuum to a volume of about 50 ml. An aliquot (2 ml) was removed for assay, and the remaining concentrate was lyophilized to give 300 mg of M43 complex.

C. Separation of M43A by Analytical HPLC

A portion of M43 complex, prepared as described in Section B, was dissolved in water at a concentration of 10 mg/ml. The solution was adjusted to pH 2.3 to increase the solubility of the complex, and the suspension was then centrifuged. The supernatant was examined by analytical HPLC, using the following conditions:

Column: 4.6-×250-mm stainless steel, prepacked by Altex
Packing: Ultrasphere ODS—5 micron
Solvent:
  A—CH$_3$CN:0.05 M KH$_2$PO$_4$ (1:9) pH 3.2
  B—CH$_3$CN:0.05 M KH$_2$PO$_4$ (2:8) pH 3.2
Gradient: 0 percent B for 15 min;, 0→40 percent B for 15–35 min;, 40 percent B for 35–38 min;, re-equilibrate in 0 percent B until 45 min.
Flow Rate: 1.0 ml/min. Chart Speed: 120 secs/cm
Detection: LDC Spectromonitor III at 280 nm
Sensitivity: 0.1 AUFS
Pumps: LDC Constametric III p System controlled by LDC Chromatograph Control Module (CCM)
Sample volume: 10 μl Peak areas were measured by the CCM; then the normalization method of integration was used to give area-percent values for each peak. M43 complex contained M43A (area percent=39.1) and vancomycin (area percent 15.1) and many additional minor factors. Thus, the ratio of antibiotic M43A to vancomycin produced by *N. orientalis* NRRL 2450, as measured by this experiment, was 2.6:1.

D. Alternate Separation of M43A by Analytical HPLC

M43 complex is examined by analytical HPLC, using the following system:

| Column: | Beckman Ultrasphere (5μ particle size), ODS, 25 cm |
|---|---|
| Mobile Phase: | Solvent A: CH$_3$CN/TEAP (5:95) |
| | Solvent B: CH$_3$CN/TEAP (2:3) |
| | [TEAP = 0.5% aqueous triethylamine adjusted to pH 3 with conc. phosphoric acid] |
| Gradient: | 9% B to 70% B over a 40-min period; then hold for 5 min. at 70% B |
| Flow Rate: | 1.0 ml/min. |
| Detection: | UV at 254 nm |

| M43A Factor | Retention Time (min.) |
|---|---|
| A51568 factor B[a] | 5.92 |
| A51568 factor A | 8.96 |
| vancomycin | 12.23 |
| desvancosamine-A51568A | 17.59 |
| M43D | 19.96 |
| desvancosamine-vancomycin[a] | 20.38 |
| M43A | 24.26 |
| M43B[a] | 25.46 |
| M43C[a] | 29.58 |
| agluco-A51568A | 36.97 |
| aglucovancomycin | 37.72 |
| agluco-M43A | 39.79 |

[a]trace amount

E. Recommended Isolation Procedure for M43A

The following procedure is recommended for isolating antibiotic M43A from M43A complex:

I. Chromatograph M43A complex over highly porous polymer (Diaion HP-20, Mitsubishi Chemical Industries, Ltd., Tokyo, Japan):
  (1) Wash with water and discard the water wash;
  (2) Wash with 50% aqueous CH$_3$CN and discard this wash;
  (3) Wash with 50% aqueous CH$_3$CN containing 0.1% CH$_3$COOH; this eluate contains the M43A.
II. Chromatograph the M43A-containing eluate (3) over reversed-phase silica gel C$_{18}$ resin to separate M43A from the remaining factors.
III. Chromatograph the separated M43A over HP-20 polymer to desalt the antibiotic, giving pure antibiotic M43A.

EXAMPLE 3

Antibiotic M43A prepared according to the method of Example 2, but using the following production medium:

| Ingredient | Amount (g/L.) |
|---|---|
| Glucose | 10 |
| Yeast | 5 |
| Distillers solubles | 5 |
| KCl | 4 |
| CaCO$_3$ | 1 |
| Tap H$_2$O | q.s. to 1 liter |

EXAMPLE 4

M43A prepared by the method of Example 2, but using the following production medium:

| Ingredient | Amount |
|---|---|
| Casamino acids | 5 g/L |
| Dextrin | 5 g/L |
| Glycerol | 5 g/L |
| Blackstrap molasses | 10 g/L |
| Yeast | 5 g/L |
| K$_2$HPO$_4$ | 1 g/L |
| Mineral Stock | 5 ml |

-continued

| Ingredient | Amount |
|---|---|
| Tap H₂O | q.s. to 1 liter |

EXAMPLE 5

M43A prepared by the method of Example 2, but using the following production medium:

| Ingredient | Amount (g/L.) |
|---|---|
| Soybean meal | 15 |
| Casein | 1 |
| NaNO₃ | 3 |
| Glucose syrup | 20 |
| Tap H₂O | q.s. to 1 liter |

EXAMPLE 6

M43A Tablet Formulation

Preparation of tablets containing 250 mg of M43A:

| Ingredient | Weight |
|---|---|
| M43A diphosphate | 282.9 mg |
| Microcrystalline cellulose | 101.1 mg |
| Croscarmellose sodium | 12.0 mg |
| Providone | 12.0 mg |
| Magnesium stearate | 3.0 mg |
| Stearic acid | 4.0 mg |
| Purified water | 0.16 ml |

Add M43A diphosphate, a portion of the microcrystalline cellulose and a portion of the croscarmellose sodium to a suitable container and blend until homogenous. Prepare a solution of Povidone in water, and add the Povidone solution to the blended powders. Granulate the resulting mixture, size if necessary and dry. Add the remaining microcrystalline cellulose and croscarmellose sodium to the dried mixture and blend. Add magnesium stearate and stearic acid, and blend the mixture. Compress the resulting powder blend into tablets with a theoretical weight of 415 mg. Each tablet contains M43A diphosphate equivalent to 250 mg of M43A.

EXAMPLE 7

M43A Capsule Formulation

| Ingredient | Weight |
|---|---|
| M43A dihydrochloride | 262.2 mg |
| Corn starch flowable powder | 137.65 mg |
| Silicone fluid 350 centistokes | 2.75 mg |
| Corn starch | 147.1 mg |

Blend M43A dihydrochloride, starch flowable powder, silicone fluid 350 centistokes and starch powder in a suitable mixer until homogeneous. Fill into appropriate size hard gelatin capsules to a net fill weight of 550 mg. Each capsule contains M43A dihydrochloride equivalent to 250 mg of M43A.

EXAMPLE 8

M43A Suspension Formulation

Prepare a sterile insoluble form of M43A by crystallization or precipitation. Mill or screen to a particle size suitable for suspension. Suspend the M43A in the following vehicle.

| Ingredient | Amount |
|---|---|
| Lecithin | 1% |
| Sodium citrate | 2% |
| Propylparaben | 0.015% |
| Water for Injection | q.s. to desired volume |

The suspension may be manufactured in bulk and filled into vials or may be prepared extemporaneously by adding the vehicle to the M43A in the vial.

We claim:

1. Antibiotic M43A which has the formula

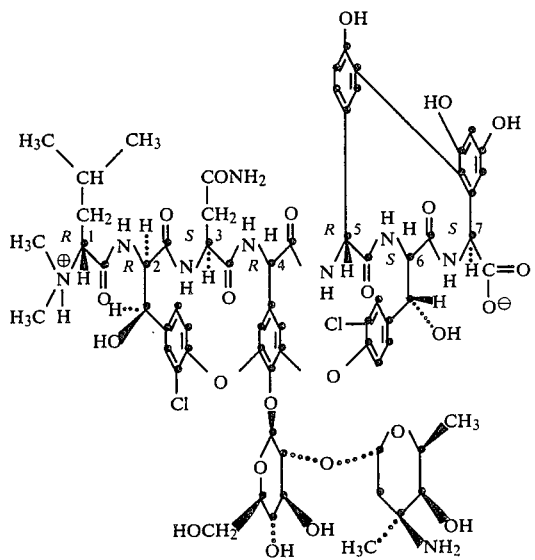

in substantially pure form and its salts.

2. A salt of claim 1 which is pharmaceutically acceptable.

3. A compound of claim 1 wherein the salt is a phosphate salt.

4. A compound of claim 1 wherein the salt is a hydrochloride salt.

5. A composition useful for treating gram-positive bacterial infections comprising an effective antibacterial amount of substantially pure antibiotic M43A, or a pharmaceutically acceptable salt of M43A, together with a suitable vehicle.

6. A method for treating infections caused by gram-positive bacteria which comprises administering an effective amount of a composition of claim 5 to an animal.

* * * * *

UNITED STATES PATENT AND TRADEMARK OFFICE
CERTIFICATE OF CORRECTION

PATENT NO. : 4,548,925
DATED : October 22, 1985
INVENTOR(S) : Harvey M. Higgins, Jr., Kurt E. Merkel and Mack H. McCormick It is certified that error appears in the above—identified patent and that said Letters Patent is hereby corrected as shown below:

Column 16, that part of the structural formula reading

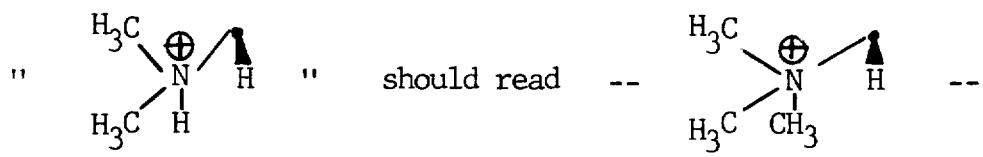

Column 16, that part of the structural formula reading

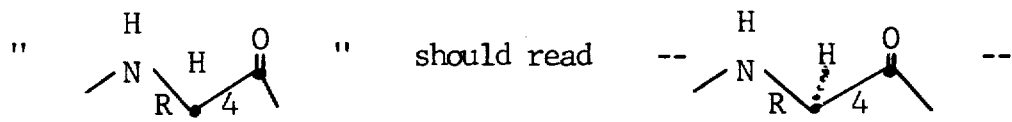

Column 16, that part of the structural formula reading

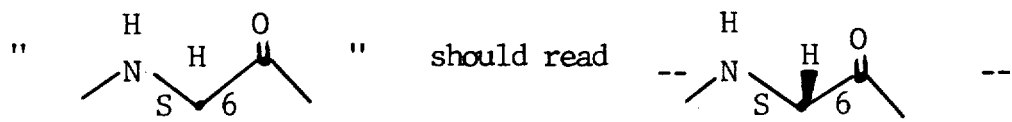

Signed and Sealed this

Sixth Day of May 1986

[SEAL]

Attest:

DONALD J. QUIGG

Attesting Officer     Commissioner of Patents and Trademarks